United States Patent [19]

Sonoyama et al.

[11] 3,959,076

[45] May 25, 1976

[54] PROCESS FOR PRODUCING 2-KETO-L-GULONIC ACID

[75] Inventors: Takayasu Sonoyama, Sakai; Hiroyoshi Tani, Moriguchi; Bunji Kageyama, Nagaokakyo; Kobee Kobayashi, Nishinomiya; Tahiko Honjo, Minoo; Shigeo Yagi, Takatsuki, all of Japan

[73] Assignee: Shionogi & Co., Ltd., Osaka, Japan

[22] Filed: Mar. 21, 1975

[21] Appl. No.: 560,885

[30] Foreign Application Priority Data

Sept. 20, 1974 Japan.............................. 49-109316

[52] U.S. Cl. ................................................ 195/30
[51] Int. Cl.$^2$............................................ C12D 1/02
[58] Field of Search ....................................... 195/30

[56] References Cited

UNITED STATES PATENTS

| | | | |
|---|---|---|---|
| 2,741,577 | 4/1956 | Shoemaker............................ | 195/30 |
| 3,234,105 | 2/1966 | Motizuki et al........................ | 195/47 |

*Primary Examiner*—Alvin E. Tanenholtz
*Attorney, Agent, or Firm*—Stewart and Kolasch, Ltd.

[57] ABSTRACT

2-Keto-L-gulonic acid is prepared from 2,5-diketo-D-gluconic acid through microbial conversion. The 2-keto-L-gulonic acid producing microorganism available for this microbial conversion includes strains which belong to the genus Corynebacterium. The incubation of the microorganism in a medium containing 2,5-diketo-D-gliconic acid as well as the direct contact of any products obtained from the microbial cells with a substrate containing said 2,5-diketo-D-gluconic acid may be used in the disclosed process.

11 Claims, No Drawings

PROCESS FOR PRODUCING 2-KETO-L-GULONIC ACID

BACKGROUND OF THE INVENTION

1. Field of the invention

The present invention generally relates to an improvement in the production of 2-keto-L-gulonic acid. More particularly, it concerns a method of preparation of said acid from 2,5-diketo-D-gluconic acid through microbial conversion.

2. Description of the Prior Art

The 2-keto-L-gulonic acid which is useful as an intermediate for synthesizing L-ascorbic acid has hithertofore been commercially produced by the so-called "Reichstein's method", which is known as a technically established process.

This method, however, comprises a number of complex steps and therefore any improvement in the overall yeild is very difficult if not completely impossible. There has hitherto been a number of proposals which contemplate a reduction in the number of steps and/or an improvement in the overall yeild.

For instance, a biochemical method wherein the 5-keto-D-gluconic acid is reduced to obtain selectively L-idonic acid which is subsequently oxidized to 2-keto-L-gulonic acid, a method of direct microbial conversion of L-sorbose into 2-keto-L-gulonic acid and the like are already known in the art.

These proposed methods have succeeded in the reduction in the number of the steps required for the production of 2-keto-L-gulonic acid at least theoretically but unexceptionally failed in the actual improvement in the overall yield and in the feasibility or the steady operation of the total system.

Moreover, the attendant disadvantageous abundance of the resultant by-product both in terms of the kind and the quantity thereof and difficulty in the separation of the intended product from the mixture which contains the by-products, and complexity in the operation hinder the commercialization of these processes.

THE SUMMARY OF THE INVENTION

It is therefore an object of the present invention to provide a novel method of producing 2-keto-L-gulonic acid which has achieved a reduction in the number of steps required for obtaining the intended product in the prior art processes. The improvement in terms of the reduction is very significant because it leads to a beginning of a completely novel pathway directed to the production of the 2-keto-L-gulonic acid.

According to the present invention, there is provided a method for producing 2-keto-L-gulonic acid which comprises; contacting a 2-keto-L-gulonic acid-producing microorganism strain selected from the genus of Corynebacterium or any product obtained by treating cells of said strain with 2,5-diketo-D-gulonic acid or any salts thereof.

The starting material of the method of this invention is 2,5-diketo-D-gluconic acid, any salts thereof or any fermentation products which include such acid or salts, and which acid or its salts may be obtainable in a good yield by, for instance, oxidizing D-glucose by a microbial process with a strain of microorganism. In the following description, any substance including such acid or salts will be simply referred to as substrates.

The 2-keto-L-gulonic acid producing strains of microorganism employed in the method of this invention can be exemplified as those separated from soil by the present inventors, which incluudes Corynebacterium sp. ASM 3311-6 (ATCC 31081), Corynebacterium sp. ASM-20A-77 (ATCC 31090), Corynebacterium sp. ASM-T-13 (ATCC 31089), and Corynebacterium sp. ASM-K-106 (ATCC 31088).

In addition to the above, microorganisms which may be employed herein include some strains which are being preserved in a public depository (culture collection) for delivery to any one upon request such as the Institute of Fermentation, Osaka, Japan (IFO).

Of these microorganisms, those isolated from soil by the present inventors, will be described taxonomically in detail in the following paragraphs.

I. ASM-3311-6 strain, ATCC No. 31081.
  A. Observations:
    1. Shape of cell (bouillon agar slant and bouillon broth at 30°C for 2 days): Rods of 0.8–1.0 × 1.2–2.1 $\mu$ with rounded ends, occurring singly or in pairs. Snapping division is found. Pleomorphism; branching and club type are observed in the respective phases of growth.
    2. Motility: Motile with single flagellum.
    3. Spore: Not formed.
    4. Gram-staining (bouillon agar slant, at 30°C for 7 days): Positive.
    5. Acid-fast: Negative.
  B. Growth on various media:
    1. Bouillon agar colonies (30°C, 24–48 hrs.): Circular, smooth, entire, unbonate, glistening translucent and vivid reddish yellow.
    2. Bouillon agar slant (30°C, 24–72 hrs.): Growth abundant, filiform, butyrous and bright reddish yellow.
    3. Bouillon broth (30°C, 7 days): Slightly turbid, flocculent sediment; on and after 5th day of the culture, ringed surface growth along the test tube wall is found. No odor.
    4. Bouillon gelatin stab (20°C and 30°C): Liquefaction; at 20°C, liquefaction is observed on and after 6th day but its progress is very slow and becomes stratiform on and after 16th day, approximately 5 mm in depth; at 30°C, liquefaction is more remarkable and proceeds more rapidly.
    5. Litmus milk (30°C, 25 days): Unchanged.
    6. Potato slant (30°C, 14 days): Growth abundant, filiform, glistening and vivid yellowish orange.
  C. Physiological properties (unless otherwise indicated, based on the results of the observations at 30°C within 14 days):
    1. Nitrite: Not produced from nitrate.
    2. Denitrification (Paraffin-sealed bouillon broth containing 1% $KNO_3$): Not observed.
    3. Methyl-red test: Negative
    4. Voges-proskauer reaction: Negative.
    5. Indole: Not produced.
    6. Hydrogen sulfide: Produced.
    7. Ammonia: Not produced.
    8. Starch: Hydrolyzed.
    9. Growth on citrate media:
      i. Koser's medium: No growth.
      ii. Simmons' medium: No growth.
      iii. Christensen's medium; Growth.
    10. Growth with inorganic nitrogen sources:
      i. Ammonium (Glucose-Hucker's medium*): Growth.
      ii. Nitrate (Glucose-Dimmick's medium*): Growth.

* A vitamin mixture is added.
11. Pigment: Not produced.
12. Urease: Negative.
13. Catalase: Positive.
14. Oxidase (Bouillon agar slant, 18–24 hrs., Tetramethylphenylenediamine): Positive.
15. Temperature relations:
    i. Temperature of growth (72 hrs.): 10–40°C. No growth at 5°C and 45°C.
    ii. Optimum temperature of growth (24 hrs.): 15–35°C.
16. pH relations:
    i. pH of growth (72 hrs.): 5.0–11.0.
    ii. Optimum pH of growth (24 hrs.): 8.0–9.0.
17. Oxygen requirement: Aerobic.
18. O-F test (Hugh-Leifson's method): Acid is only aerobically produced from D-glucose. Negative against lactose.
19. Production of acids and gases from sugars (Barsiekow's medium):
    i. Acid but no gas from L-arabinose, D-xylos, D-glucose, D-mannose, D-fructose, D-galactose, maltose, sucrose, trehalose, D-mannitol and glycerine.
    ii. Neither acid nor gas from lactose, D-sorbitol and starch.
20. Cellulose (Peptone-water + microcrystalline cellulose): Not hydrolyzed.
21. Methylene-blue (bouillon broth, 18–24 hrs.): Reduced.
22. D-gluconic acid: Utilized.
23. 2-Keto-D-gluconic acid: Utilized.
24. Lactic acid (Glucose bouillon broth, 48 and 96 hrs.): Not produced from lactose
25. Heat tolerance (10% skimmed milk solution, 72°C, 10 min.) Negative.

D. Origin: Soil.

The above taxonomical properties are compared with the description of the "Manual" to lead to the conclusion that this strain belongs to the genus of Corynebacterium in view of the following observations; being gram-positive short rods which form no spore, showing snapping division, having pleomorphism of branching and club type, being unable to hydrolyze cellulose and to produce lactic acid, and having no heat tolerance.

This strain is therefore named by the present inventors as Corynebacterium sp. No. ASM-3311-6.

II. ASM-20A-77 Strain ATCC No. 31090.

A. Observations:
1. Shape of cells (bouillon agar slants and bouillon broth at 30°C for 2 days): Rods, 0.6–0.8 by 0.9–2.1 $\mu$, occurring singly and in pairs with rounded ends. Snapping division, branching and club types are observed.
2. Motility: Non-motile.
3. Spore: Not formed.
4. Gram staining (bouillon agar slants, at 30°C for 7 days): Gram-variable.
5. Acid-fast: Negative.

B. Growth on various media:
1. Bouillon agar colonies (30°C, 24–48 hrs.): Circular, smooth, entire, convex, glistening, translucent and bright yellow.
2. Bouillon agar slant (30°C, 24–72 hrs.): Growth abundant, filiform and butyrous, and bright greenish yellow.
3. Bouillon broth (30°C, 7 days): Slight turbid; Surface pellicle growth is observed within 4 days; Flaky sediment; No odor.
4. Bouillon gelatin stab: Liquefaction: at 20°C, liquefaction is observed slightly at 14th day and then changes from infundibuliform to stratiform on extended culture; at 30°C, distinct liquefaction is observed.
5. Litmus milk (30°C, 21 days): Peptonization begins at 11th day and is completed after 3 weeks. The pH becomes slightly alkaline at the early stage of culture and then acidic at the late stage. Litmus is reduced in the lower layer. Surface pellicle growth and light yellow sediment are observed. No coagulation is observed.
6. Potato slant (30°C, 14 days): Growth abundant; bright greenish yellow glistening.

C. Physiological properties (unless otherwise indicated, based on the results of the observation at 30°C within 14 days);
1. Nitrite: Nitrite is not produced from nitrate.
2. Denitrification: Neither growth nor gas production is observed in paraffin-sealed bouillon broth containing 1% KNO$_3$.
3. Methyl-red test: Negative.
4. Voges-Proskauer reaction: Negative.
5. Indole: Not produced.
6. Hydrogen sulfide: Not produced.
7. Ammonia: Not produced.
8. Starch: Hydrolyzed.
9. Growth on citrate media:
    i. Koser's medium*: No growth.
    ii. Simmon's medium*: Growth.
    iii. Christensen's medium: Growth.
* Vitamin mixture added.
10. Growth with inorganic nitrogen sources:
    i. Ammonium (Glucose-Hucker's medium**): Growth.
    ii. Nitrite (Glucose-Dimmick's medium**): Growth.
** Vitamin mixture added.
11. Pigment: Not produced.
12. Urease: Negative.
13. Catalase: Positive.
14. Oxidase (bouillon agar slant, 18–24 hrs., tetramethylphenylenediamine): Positive.
15. Temperature relations:
    i. Temperature of growth (72 hrs): 10.0–38.0°C.
    ii. Optimum temperature of growth (24 hrs): 23.0–28.0°C.
16. pH relations:
    i. pH of growth (72 hrs): 6.0–10.0
    ii. Optimum pH of growth (24 hrs): 7.0–8.0
17. Oxygen requirement: Aerobic.
18. O-F test (Hugh-Leifson's method): Acid is only aerobically produced from D-glucose, but neither acid nor gas is produced from lactose.
19. Production of acids and gases from sugars (Barsiekow's medium):
    i. Acid but no gas from L-arabinose, D-xylose, D-glucose, D-mannose, D-fructose, D-galactose, maltose, sucrose, and starch.
    ii. Neither acid nor gas from lactose, trehalose, D-sorbitol, D-mannitol, inositol, and glycerol.
20. Cellulose (Peptone-water + microcrystalline cellulose): Not hydrolyzed.
21. Methylene-blue (bouillon broth, 18–24 hrs.): Reduced.

22. D-gluconic acid: Utilized.
23. 2-Keto-D-gluconic acid: Slightly utilized.

III. ASM-T-13 Strain ATCC 31089

A. Observations:
1. Shape of cells (bouillon agar slants and bouillon broth at 30°C for 2 days): Rods, 0.8–0.9 by 1.0–1.3 $\mu$, occurring singly and in pairs with rounded ends. Snapping division, branching and club types are observed.
2. Motility: Non-motile.
3. Spore: Not formed.
4. Gram staining (bouillon agar slants, at 30°C for 7 days): Positive.
5. Acid-fast: Negative.

B. Growth on various media:
1. Bouillon agar colonies (30°C, 24–48 hrs.): Circular, smooth, entire, convex, glistening, translucent, and light yellowish orange.
2. Bouillon agar slants (30°C, 24–72 hrs.): Growth moderate, filiform, butyrous, and light reddish yellow.
3. Bouillon broth (30°C, 7 days): Slight turbid; No surface growth is observed; Flocculent to flaky sediment; No odor.
4. Bouillon gelatin stab: No liquefaction.
5. Litmus milk (30°C, 21 days): Unchanged within 4 days. After 8 days, becoming alkaline, and very weakly coagulated. On and after 16th day litmus completely and uniformly reduced. Very weakly peptonized and not coagulated.
6. Potato slant (30°C, 14 days): Growth moderate; bright yellow glistening.

C. Physiological properties (unless otherwise indicated, based on the results of the observation at 30°C within 14 days):
1. Nitrite: Nitrite is not produced from nitrate.
2. Denitrification: Neither growth nor gas production is observed in paraffin-sealed bouillon broth containing 1% KNO$_3$.
3. Methyl-red test: Negative.
4. Voges-Proskauer reaction: Negative.
5. Indole: Not produced.
6. Hydrogen sulfide: Not produced.
7. Ammonia: Not produced.
8. Starch: Weakly hydrolyzed.
9. Growth on citrate media:
   i. Koser's medium*: No growth.
   ii. Simmon's medium*: No growth.
   iii. Christensen's medium: Growth.
* Vitamin mixture added.
10. Growth with inorganic nitrogen sources:
   i. Ammonium (Glucose-Hucker's medium**): No growth.
   ii. Nitrate (glucose-Dimmick's medium**): No growth.
** Vitamin mixture added.
11. Pigment: Not produced.
12. Urease: Negative.
13. Catalase: Positive.
14. Oxidase (bouillon agar slant, 18–24 hrs., tetramethylphenylenediamine): Positive.
15. Temperature relations:
   i. Temperature of growth (72 hrs): 10.0–38.0°C.
   ii. Optimum temperature of growth (24 hrs): 23.0–28.0°C.
16. pH relations:
   i. pH of growth (72 hrs): 6.0–8.0.
   ii. Optimum pH of growth (24 hrs): 7.0–8.0.
17. Oxygen requirement: Aerobic.
18. O-F test (Hugh-Leifson's method): Acid is slightly produced both aerobically and anaerobically from D-glucose*, but neither acid nor gas is produced from lactose.

*(The top layer of paraffin-sealed stab-culture turns yellow as normal stab-culture).

19. Production of acids and gases from sugars (Barsiekow's medium):
   i. Acid but no gas from L-arabinose, D-xylose, D-glucose, D-mannose, D-fructose, D-galactose, maltose, lactose, trehalose, D-sorbitol (weak), D-mannitol, sucrose, and glycerol.
   ii. Neither acid nor gas from inositol, and starch.
20. Cellulose (Peptone-water + microcrystalline cellulose): Not hydrolyzed.
21. Methylene-blue (bouillon broth, 18–24 hrs.): Not reduced.
22. D-gluconic acid: Slightly utilized.
23. 2-Keto-D-gluconic acid: Slightly utilized.

IV. ASM-K-106 Strain, ATCC 31088

A. Observations:
1. Shape of cells (bouillon agar slants and bouillon broth at 30°C for 2 days): Rods, 0.6–0.7 by 1.0–1.3 $\mu$, occurring singly and in pairs with rounded ends. Snapping division, branching and club types are observed.
2. Motility: Non-motile.
3. Spore: Not formed.
4. Gram staining (bouillon agar slants, at 30°C for 7 days): Positive.
5. Acid-fast: Negative.

B. Growth on various media:
1. Bouillon agar colonies (30°C, 24–48 hrs.): Circular, smooth, entire, raised, glistening, translucent, and bright yellow.
2. Bouillon agar slant (30°C, 24–48 hrs.): Growth abundant, filiform and butyrous, and bright greenish yellow.
3. Bouillon broth (30°C, 7 days): Slight turbid; Surface pellicle growth is observed within 4 days; Flaky sediment; No odor.
4. Bouillon gelatin stab: Liquefaction: At 20°C, liquefaction is observed slightly at 14th day and then changes from infundibuliform to stratiform on extended culture; at 30°C, distinct liquefaction is observed.
5. Litmus milk (30°C, 21 days): Peptonization begins at 11th day and is completed after 3 weeks. The pH becomes slightly alkaline at the early stage of culture and then acidic at the late stage. Litmus is reduced in the lower layer. Surface pellicle growth and light yellow sediment are observed. No coagulation is observed.
6. Potato slant (30°C, 14 days): Growth abundant; bright yellow glistening.

C. Physiological properties (unless otherwise indicated, based on the results of the observation at 30°C within 14 days):
1. Nitrite: Nitrite is produced from nitrate.
2. Denitrification: Neither growth nor gas production is observed in paraffin-sealed bouillon broth containing 1% KNO$_3$.
3. Methyl-red test: Negative.
4. Voges-Proskauer reaction: Negative.
5. Indole: Not produced.
6. Hydrogen sulfide: Not produced.
7. Ammonia: Not produced.

8. Starch: Hydrolyzed.
9. Growth on citrate media:
   i. Koser's medium*: No growth.
   ii. Simmon's medium*: Growth.
   iii. Christensen's medium: Growth.
* Vitamin mixture added.
10. Growth with inorganic nitrogen sources:
   i. Ammonium (Glucose-Hucker's medium**): Growth.
   ii. Nitrate (Glucose-Dimmick's medium**): Growth.
** Vitamin mixture added.
11. Pigment: Not produced.
12. Urease: Negative.
13. Catalase: Positive.
14. Oxidase: (bouillon agar slant, 18–24 hrs., tetramethylphenylenediamine): Positive.
15. Temperature relations:
   i. Temperature of growth (72 hrs): 10.0–38.0°C
   ii. Optimum temperature of growth (24 hrs): 23.0–30°C.
16. pH relations:
   i. pH of growth (72 hrs): 6.0–9.0
   ii. Optimum pH of growth (24 hrs): 7.0
17. Oxygen requirement: Aerobic.
18. O-F test (Hugh-Leifson's method): Acid is slightly produced both aerobically and anaerobically from D-glucose*, but neither acid nor gas is produced from lactose.
*(The top layer of paraffin-sealed stab-culture turns yellow as normal stab-culture.)
19. Production of acids and gases from sugars (Barsiekow's medium):
   i. Acid but no gas from L-arabinose, D-xylose, D-glucose, D-mannose, D-fructose, D-galactose, maltose, sucrose, lactose(weak), D-mannitol (weak), and starch.
   ii. Neither acid nor gas from trehalose, D-sorbitol, inositol, and glycerol.
20. Cellulose (Peptone-water + microcrystalline cellulose): Not hydrolyzed.
21. Methylene-blue (bouillon broth, 18–24 hrs.): Reduced.
22. D-gluconic acid: Utilized.
23. 2-Keto-D-gluconic acid: Slightly utilized.

The taxonomical properties of the above three strains are compared with the description of the "Manual" to lead to the conclusion that these strains belong to the genus of Corynebacterium in view of the observations which are identical with that of the previously described ASM-3311-6 strain.

Any mutated or modified strains obtained by artificially or inductively mutating the aforedefined microorganism strains, with a treatment by means of, for instance, ultraviolet or X-ray irradiation, or a mutating agent such as nitrogen mustard, may likewise be utilized in the method of this invention with advantage.

In the method of this invention, the aforedescribed strains may be inoculated with and incubated in a medium which includes the aforedefined substrate and the cells of such strain, for instance, resting cells or any processed product obtained from the cells may be used to act directly on the substrate. Any means per se known in connection with the incubation technique for microorganisms may be adopted although the use of aerated and agitated deep-tank fermenters is particularly preferred. A preferred result may be obtainable from an incubation which utilizes a liquid broth medium.

As regards the nutrient medium available for the incubation of the microorganism, although no special restriction is imposed on its class, an aqueous nutrient medium suitably including carbon sources, nitrogen sources, other inorganic salts, small amounts of other nutrients and the like, which can be utilized by the microorganism is desirable for the advantageous incubation of the microorganism. Various nutrient materials which are generally used for the better growth of microorganisms may suitably be included in the medium.

The nitrogen source includes inorganic or organic nitrogen compounds, or compositions containing such compounds which may be exemplified by ammonium salts, nitrate salts, corn steep liquor, peptone, meat extract, bean powder, wheat gluten, yeast extract, yeasts and urea.

The carbon sources which may be included in the medium as the substrate can be exemplified as polyhydric alcohols or sugars such as glucose, glycerol, sucrose, lactose, dextrine, maltose and molasses in addition to the starting material, 2,5-diketo-D-gluconic acid.

Salts of, for instance, calcium, magnesium, potassium, zinc, copper, iron and other metals are employed as the inorganic salts.

For the advantageous performance of the incubation, any suitable factor which can promote the formation of the end product may be added to the medium.

The mixing ratio of these nutrients and the amounts of each ingredient may vary with the generic property of the strain employed and the amounts of the starting material, 2,5-diketo-D-gluconic acid, and the other attendant conditions of the incubation may be selected or determined in accordance with the particulars of the individual case.

Although the concentration of 2,5-diketo-D-gluconic acid in the medium may also be varied with the generic character and the like of the employed strain, a concentration of about 1–200 g/l is generally applicable and, inter alia, a concentration of about 1–50 g/l is preferred.

The conditions of the incubation may also vary with the species and generic character of the strain employed, the composition of the medium and other attendant factors, and may, of course, be selected or determined in accordance with the particulars of the individual cases in order to yield the intended product most efficiently, although an incubation temperature of about 20°–35°C and a pH value of the medium of about 4–9 may preferably be maintained. Normally, an incubation period ranging from 10 hours to 100 hours may be sufficient and the formation of the intended product in the medium reaches its maximum value within such period.

In order to maintain the pH value of the medium to that most suitable for the enzymatic activity of the substance which is produced by the microorganism, any suitable acidic or basic agent may be added to the medium in a suitable amount at a suitable time during the incubation. The same object may alternatively be accomplished by initially incorporating a suitable buffer into the medium at the beginning of the incubation.

The required total amount of the starting material, 2,5-diketo-D-gluconic acid, may be incorporated in the medium all at once at the beginning of the incubation or may be added to the medium in portions at any time during the incubation.

In addition to the previously-described incubation of the microorganism strain, the process of the present invention affords another means wherein the cells of the microorganism, i.e., resting cells, acetone treated cells, cells of lyophilized strains, the ground product thereof and the like are contacted directly with the substrate containing the starting material, 2,5-diketo-D-gluconic acid.

In such cases of direct contact of the cells or the processed product thereof with the substrate, the conditions of the temperatures, pH values and the like being the same as or similar to the case of the incubation of the strain itself, may be employed. Furthermore, any buffer solution may suitably be used to maintain the pH value of the substrate constant.

The amount of the cells or the processed product thereof employed in this direct contact method, may desirably be sufficient for converting the total amount of the starting material, 2,5-diketo-D-gluconic acid in the substrate into the intended product, 2-keto-L-gulonic acid.

The 2-keto-L-gulonic acid thus formed and accumulated in the medium may be separated and purified by any per se known suitable means which utilizes the property of the product, and it may be separated as the free acid or as a salt of sodium, potassium, calcium, ammonium or the like.

In the case wherein the 2-keto-L-gulonic acid is obtained in its free state, it may be converted into any salts of, for instance, sodium, potassium, calcium, ammonium or the like by any suitable per se known means, while if the process yields a salt, the salt may be converted into its free acid or into any other salts by any suitable means.

Any methods as may be available for the separation of the intended product from the medium can be employed unless the method used would deteriorate the object of the present invention. For instance, the separation may be performed in any suitable combination or repetition of the following unit processes; a) removal of the cells of the microorganisms from the fermented broth by filtration, centrifugation or treatment with active charcoal, b) precipitation of the intermediate crystals by concentrating the filtered broth, c) recovery of the precipitated crystals by filtrating or centrifuging the concentrated broth, d) recrystallization of the intermediate crystals, e) extraction with solvent, and f) fractionation by chromatography.

The identification of the 2-keto-L-gulonic acid obtained by the method of this invention may be performed by, for instance, elemental analysis as well as measurement of physicochemical properties such as melting point, spectrum of infrared absorption, optical rotation and the like.

Description of the Preferred Embodiments

In the following, the process of the present invention will be illustrated in more detail by way of examples wherein mixtures obtained by mixing an aqueous solution of salts of 2,5-diketo-D-gluconic acid wherein any microorganisms have been removed by filtration with a liquid containing the remainder of the required ingredients after both liquids have been cooled are used as substrates because of the poor heat-stability of said salts.

In a commercial scale operation, the employment of a more pertinent, effective and safe procedure of sterilization, for instance, continuous heat sterilization or filtration by a micro-filter is, however, recommended In the following examples, two kinds of 2,5-diketo-D-gluconic acid solutions were used as the substrate.

One was a 5 percent aqueous solution prepared from the powder of calcium 2,5-diketo-D-gluconate and the other was a cell-free broth of calcium 2,5-diketo-D-gluconate fermented by Acetomonas albosesamae ATCC No. 21998 from D-glucose. A taxonomical description of the strain is briefly stated as follows:

*Acetomonas albosesamae* (Wakisaka) ATCC No. 21998
A. Observations:
  1. Shape of cells (Glucose-Yeast extract agar slant at 28°C for 3 days): Rods 0.6–0.8 by 1.2–3.5 $\mu$, with rounded ends occurring singly and in slimy masses. No pleomorphism but some filamentous form is observed.
  2. Motility (Glucose-bouillon broth and soft agar at 30°C for 24 hours): Motile with subpolar flagellum. Many of the cells lack flagellum.
  3. Spore (Glucose-Yeast extract agar slant at 28°C for 7 days): Not formed.
  4. Gram staining (Glucose-Yeast extract agar slant at 28°C for 12, 20, 36 and 72 hours): Negative.
  5. Acid-fast staining (Glucose-Yeast extract agar slant at 28°C for 72 and 360 hours): Negative.
B. Growth on various media:
  1. Agar colonies (Glucose-Yeast extract agar at 28°C for 1–3 days): Circular, convex, entire colonies of smooth surface, translucent to opaque density, grayish white in color and brittle to butyrous consistency.
  2. Agar slant (Glucose-Yeast extract agar at 28°C for 1–3 days): Moderate, filiform, brittle to butyrous structure, grayish-white color growth of dull shining surface and translucent to a little opaque optical density. No diffusible pigment is observed at early stage but slightly pale yellowish brown pigment is observed at late stage.
  3. Growth in broth (Emerson's medium at 28°C for 1–3 days): Moderate, flocculent growth on the upper layer at early stage. No pellicle formation.
  4. Bouillon gelatin stab (at 27°C for 1–30 days): Scanty growth and no liquefaction.
  5. Litmus milk: Rapid acidification with reduction of the litmus. No peptonization is observed.
C. Physiological properties (unless otherwise indicated, based on the results of the observation at 28°C for 1–7 days):
  1. Nitrite: Nitrite is produced from nitrate.
  2. Methyl-red reaction: Positive.
  3. Voges-Proskauer's reaction: Negative.
  4. Indole: Not produced.
  5. Hydrogen sulfide (lead paper method): Produced.
  6. Starch: Not hydrolyzed.
  7. Utilization of citrate as a sole source of carbon (Simmon's medium at 28°C for 1–3 days): No growth.
  8. urease (at 28°C for 1–3 days: Positive.
  9. Catalase (Glucose-Yeast extract agar slant at 28°C for one day): Positive.
  10. Temperature for growth (Emerson's medium for one day): Growth at 10°C to 45°C. Optimum 25°–35°C.
  11. pH for growth (Glucose-Bouillon broth at 28°C for one day): Optimum pH for growth: 6.0–8.0. Does not grow at pH 2.55 but grows slightly at pH 4.38.

12. Oxygen requirement (Mannitol-Yeast extract soft agar at 28°C for 3 days): Aerobic.
13. Production of acids and gases from sugars:
   i. Acid but no gas from : L-arabinose, D-xylose, L-raffinose, D-glucose, D-mannose, D-galactose, D-fructose, maltose, lactose, glycerol, mannitol, sorbitol, and salicine. Acid production from sorbitol is weak.
   ii. Neither acid nor gas from: sucrose, starch and inulin.
14. Production of acid from ethanol (Yeast extract-peptone at 27°C): Very weak acid production is observed in 1.92% ethanol containing medium but no acid forms at 3.5 and 7.5%.

The scrutinization of the above physiological properties is made, unless otherwise specified, on the basis of the description in "Manual of Microbiological Methods, 1957 McGraw-Hill Book Co. Inc." edited by the Society of American Bacteriologists.

Example 1

The strains described in Table 1 were used.

One loopful of an organism from a bouillon slant was inoculated into a 500 ml shaker flask containing 100 ml of seed medium and incubated on a rotary shaker (240 rpm).

The seed medium contained 0.2% of glycerine, 0.2% of yeast extract, 0.2% of polypeptone, 0.1% of potassium phosphate, monobasic and 0.02% of magnesium sulfate·7H$_2$O. The pH of the seed medium was adjusted to 7.0 before sterilization (115°C, 20 min.).

After incubation at 30°C for 15 hours, 5 ml of this seed culture was transferred into 50 ml of a fermentation medium in a 500 ml shaker flask.

The fermentation medium contained 0.2% of D-glucose, 0.4% of yeast extract, 0.4% of polypeptone, 0.2% of potassium phosphate, monobasic and 0.4% of magnesium sulfate·7H$_2$O. The pH of the medium was adjusted to 7.0 before sterilization (115°C, 20 min.).

The above mentioned two kinds of 2,5-diketo-D-gluconic acid solution were then added to this fermentation medium, respectively, before the medium was incubated or after the medium was incubated for 24 hrs. The 2,5-diketo-D-gluconic acid solutions were sterilized by filtration. The concentration of 2,5-diketo-D-gluconic acid in the fermentation broth was 2.5%. The incubation was performed on a rotary shaker for 72 hours at 30°C, after the 2,5-diketo-D-gluconic acid solution was added thereto.

The broth was analyzed by means of gas chromatography (Column, silicone gum SE-52; Sample, silylated) and paper chromatography (solvent, phenol: formic acid: water, 75:4:25; Reagent, Aniline hydrogen phthalate).

The results are summarized in Table 1.

In each case the formation of 2-keto-D-gluconic acid was observed.

Table 1

| Time of Addition before incubation (hr) | Kind of 2,5-diketo-D-gluconic acid soln. | | | |
|---|---|---|---|---|
| | Calcium salt | | Broth of Acetomonas albosesamae | |
| | 2KLG* | 2KDG** | 2KLG* | 2KDG** |
| Corynebacterium sp. ASM-3311-6 ATCC 31081 | 0 | 0.18 | 0.59 | 0.23 | 0.07 |
| | 24 | 0.95 | 0.74 | 1.18 | 1.04 |
| Corynebacterium sp. ASM-20A-77 | 0 | 1.47 | 0.15 | 1.58 | 0.19 |

Table 1-continued

| Time of Addition before incubation (hr) | Kind of 2,5-diketo-D-gluconic acid soln. | | | |
|---|---|---|---|---|
| | Calcium salt | | Broth of Acetomonas albosesamae | |
| | 2KLG* | 2KDG** | 2KLG* | 2KDG** |
| ATCC 31090 | 24 | 3.55 | 0.24 | 3.67 | 0.28 |
| Corynebacterium sp. ASM-K-106 | 0 | 0.88 | 0.21 | 0.95 | 0.18 |
| ATCC 31088 | 24 | 2.61 | 0.17 | 2.85 | 0.21 |
| Corynebacterium sp. ASM-T-13 | 0 | 0.46 | Trace | 0.56 | 0.11 |
| ATCC 31089 | 24 | 1.23 | 0.05 | 1.31 | 0.11 |

*Accumulation of 2-keto-L-gulonic acid (mg/ml)
**Accumulation of 2-keto-D-gluconic acid (mg/ml)

EXAMPLE 2

The strains presented in Table 2 were used and the cells were prepared by a procedure similar to that described in Example 1. The 2,5-diketo-D-gluconic acid broth of Acetomonas albosesamae was added to the fermentation medium after the medium was incubated for 24 hours.

After the incubation for another 24 hours, the cells were collected, washed twice with sterilized saline, and suspended in 0.05 M of Tris buffer (pH 7.5).

The concentration of cells was adjusted to 4.1 mg (dry weight) per ml.

Calcium 2,5-diketo-D-gluconate was added to 100 ml of this cell suspension and its concentration was 1%.

During the incubation for 24 hrs at 30°C by shaking, samples were withdrawn at given intervals, and were analyzed by the same means of gas chromatography and paper chromatography as described in Example 1.

2-Keto-L-gulonic acid was accumulated from the beginning of the reaction. The final results are summarized in Table 2. In each case, small amounts of 2-keto-D-gluconic acid were observed.

Table 2

| Strains | Amounts of 2-keto-L-gulonic acid after the reaction |
|---|---|
| ASM 3311-6, ATCC 31081 | 0.64 mg/ml |
| ASM 20A-77, ATCC 31090 | 1.85 " |
| ASM K-106, ATCC 31088 | 1.32 " |
| ASM T-13, ATCC 31089 | 0.55 " |

What is claimed is:

1. A process for producing 2-keto-L-gulonic acid or a salt thereof which comprises cultivating a 2-Keto-L-gulonic acid producing microorganism selected from the group consisting of the genus Corynebacterium, and mutants thereof, in an aqueous nutrient medium in the presence of 2,5-diketo-D-gluconic acid or salts thereof, and recovering the produced 2-keto-D-gulonic acid or salts thereof from the resultant mixture.

2. A process as claimed in Claim 1, wherein said microorganism is Corynebacterium sp. ASM-3311-6 ATCC 31081.

3. A process as claimed in Claim 1, wherein said microorganism is Corynebacterium sp. ASM-20A-77 ATCC 31090.

4. A process as claimed in Claim 1, wherein said microorganism is Corynebacterium sp. ASM-T-13 ATCC 31089.

5. A process as claimed in Claim 1, wherein said microorganism is Corynebacterium sp. ASM-K-106 ATCC 31088.

6. A process for producing 2-keto-L-gulonic acid or a salt thereof which comprises; contacting a 2-keto-L-gulonic acid producing strain selected from microorganisms which belong to the genus Corynebacterium or treated cells of said microorganism strain having the enzyme activity to convert 2,5-diketo-D-gluconic acid to 2-keto-L-gulonic acid with 2,5-diketo-D-gluconic acid or a salt thereof, under conditions sufficient to produce 2-keto-L-gulonic acid, and recovering the produced 2-keto-L-gulonic acid or any salts thereof from the resulting mixture.

7. A process as claimed in Claim 6, wherein said 2-keto-L-gulonic acid producing strain is inoculated with and incubated in a medium containing 2,5-diketo-D-gluconic acid or a salt thereof to effect a fermentative action therein, and recovering 2-keto-L-gulonic acid or any salts thereof accumulated during the incubation.

8. A process as claimed in Claim 6, wherein an aqueous medium containing viable cells of said microorganism strain is contacted with a substance containing 2,5-diketo-D-gluconic acid or a salt thereof, under conditions sufficient to produce 2-keto-L-gulonic acid, and recovering said 2-keto-L-gulonic acid or any salts thereof produced and accumulated in the substance during said contact.

9. A process as claimed in Claim 6, wherein said strain or treated cells thereof are contacted with said 2,5-diketo-D-gluconic acid or salt thereof at a temperature of about 20° to 35°C. and at a pH of about 4 to 9.

10. A process as claimed in Claim 1, wherein the concentration of 2,5-diketo-D-gluconic acid or salt thereof present in said nutrient medium is about 1 to 200 g/l.

11. A process as claimed in Claim 10, wherein said microorganism is cultivated at a temperature of about 20° to 35°C. and at a pH of about 4 to 9.

\* \* \* \* \*

UNITED STATES PATENT AND TRADEMARK OFFICE
CERTIFICATE OF CORRECTION

PATENT NO. : 3,959,076
DATED      : May 25, 1976
INVENTOR(S) : Takayasu SONOYAMA et al It is certified that error appears in the above-identified patent and that said Letters Patent is hereby corrected as shown below:

Claim 1

Column 12, line 58, change "2-keto-D-gulonic" to --2-keto-L-gulonic--.

Signed and Sealed this

Eleventh Day of February 1986

[SEAL]

Attest:

DONALD J. QUIGG

Attesting Officer

Commissioner of Patents and Trademarks